United States Patent
Liu et al.

(10) Patent No.: US 9,671,371 B2
(45) Date of Patent: Jun. 6, 2017

(54) ANOMALY RECOGNITION SYSTEM AND METHODOLOGY

(71) Applicant: Schlumberger Technology Corporation, Sugar Land, TX (US)

(72) Inventors: Zhanke Liu, Sugar Land, TX (US); Shunfeng Zheng, Katy, TX (US); Mirjam Zwanenburg, Esbjerg (DK)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/318,187

(22) Filed: Jun. 27, 2014

(65) Prior Publication Data

US 2015/0377012 A1 Dec. 31, 2015

(51) Int. Cl.
*G01N 27/72* (2006.01)
*G01N 27/83* (2006.01)
*E21B 19/22* (2006.01)

(52) U.S. Cl.
CPC .......... *G01N 27/83* (2013.01); *E21B 19/22* (2013.01)

(58) Field of Classification Search
CPC .......... G01N 27/82; G01N 27/902; G01N 2291/2636; G01N 29/043; G01N 29/2412; G01N 27/87; G01N 27/9033; G01N 2291/0425; G01N 27/904; G01N 2291/2634; G01N 27/83; G01N 27/9046; G01N 2291/0422; G01N 29/30; G01N 29/46; G01N 19/00; G01N 27/90; G01N 29/2481; G01N 29/265; G01N 29/225; G01N 2291/0427; G01N 29/041; G01N 29/07; G01N 29/348; G01B 7/10; G01B 17/02; G01B 5/00; G01R 31/026; G01R 33/04; G01D 5/485; G01H 11/04; G01L 1/00; G01L 3/102; G01L 3/105; G01L 5/0047; G01V 3/104; G01V 3/28

See application file for complete search history.

(56) References Cited

U.S. PATENT DOCUMENTS

| | | |
|---|---|---|
| 6,023,986 A | 2/2000 | Smith et al. |
| 2004/0095137 A1 | 5/2004 | Kwun et al. |

(Continued)

FOREIGN PATENT DOCUMENTS

| | | |
|---|---|---|
| EP | 2725352 A1 | 4/2014 |
| WO | 2012103541 A2 | 8/2012 |
| WO | 2012174057 A1 | 12/2012 |

OTHER PUBLICATIONS

International Search Report issued in related PCT application PCT/US2015/037567 on Sep. 18, 2015, 3 pages.

*Primary Examiner* — Vinh Nguyen
(74) *Attorney, Agent, or Firm* — Michael L. Flynn; Jody Lynn DeStefanis; Robin Nava

(57) ABSTRACT

A technique facilitates anomaly recognition and tracking in a variety of components, such as tubular components. The technique comprises sensing for anomalies in the component, and storing detected anomalies in a storage medium. The detected anomalies are matched with stored digital descriptions of anomalies. The stored digital descriptions may be anomalies of similar types and/or anomalies detected on the specific component being tested. The detected anomalies are ranked according to similarities with respect to the stored digital descriptions.

20 Claims, 4 Drawing Sheets

(56) References Cited

U.S. PATENT DOCUMENTS

| | | | | |
|---|---|---|---|---|
| 2004/0216512 A1* | 11/2004 | Kwun | ............... | G01N 29/07 73/1.82 |
| 2005/0046591 A1* | 3/2005 | Pacault | ............... | E21B 47/12 340/855.2 |
| 2006/0096753 A1 | 5/2006 | Zheng et al. | | |
| 2011/0191045 A1* | 8/2011 | Boenisch | ............ | G01N 27/902 702/65 |
| 2014/0200831 A1* | 7/2014 | Smith | ............... | G01M 5/0025 702/38 |

* cited by examiner

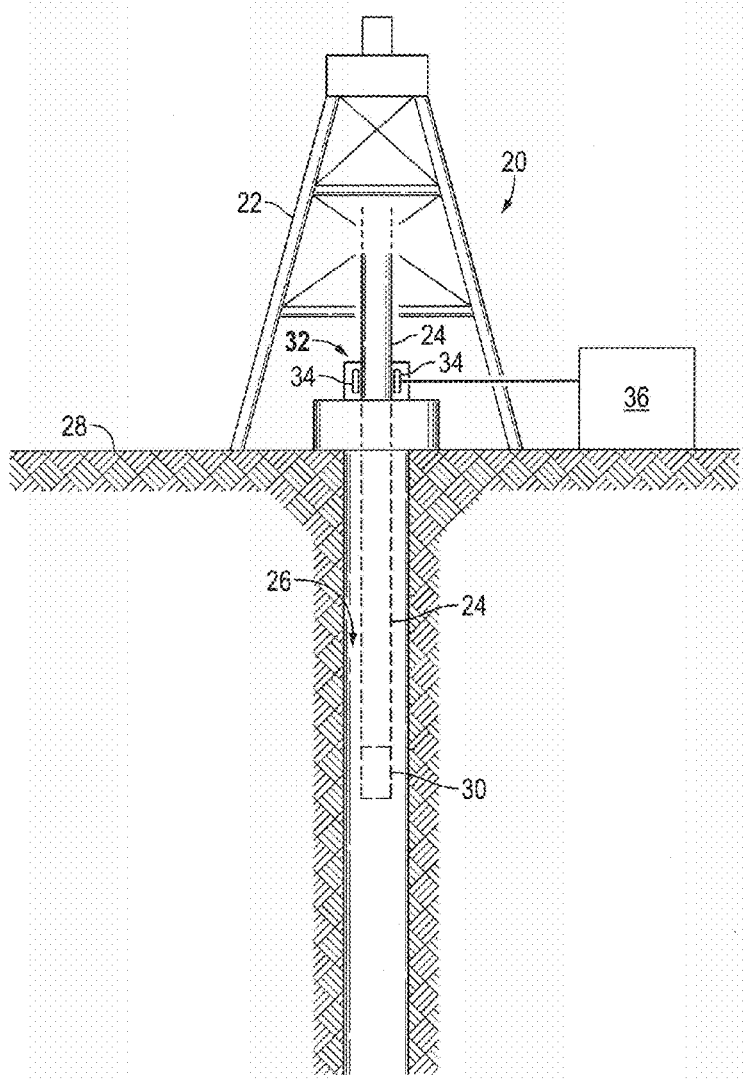

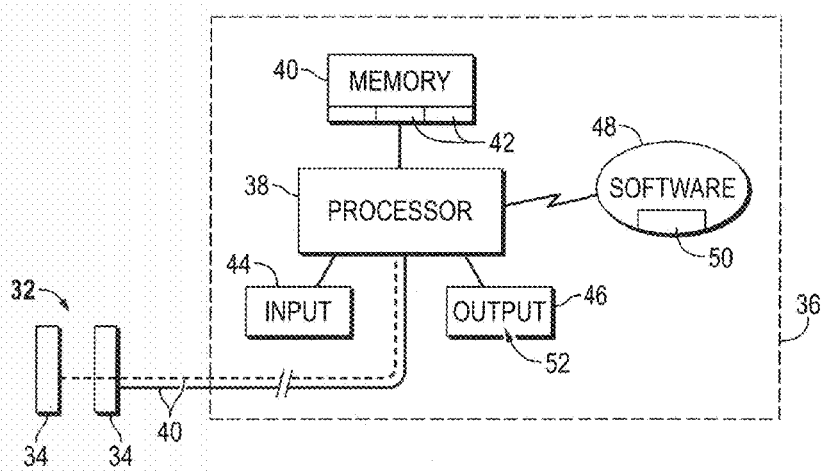

ANOMALY RECOGNITION SYSTEM AND METHODOLOGY

BACKGROUND

In many types of well applications, coiled tubing is employed for conveying downhole tools, chemicals, and/or other devices or fluids downhole. When coiled tubing is moved into and out of the borehole, the coiled tubing is subjected to bending and straightening cycles. The coiled tubing also may be subjected to high stresses due to a combination of tension, compression, pressure differentials, and/or torque. Harsh environmental factors such as chemical exposures also may have a detrimental impact on the coiled tubing. As a result, coiled tubing may be subjected to failures due to bending cycles, mechanical damage, corrosion, factory defects, and other factors affecting the integrity of the coiled tubing.

SUMMARY

In general, a methodology and system are provided for anomaly recognition and tracking in a variety of components, such as tubular components such as, but not limited, to coiled tubing utilized in well intervention operations in well operations. The technique comprises sensing for anomalies in the component, and storing detected anomalies in a storage medium. The detected anomalies are matched with stored digital descriptions of anomalies. The stored digital descriptions may comprise anomalies of similar types and/or anomalies previously detected on the specific component being tested. The detected anomalies are ranked according to similarities with respect to the stored digital descriptions.

However, many modifications are possible without materially departing from the teachings of this disclosure. Accordingly, such modifications are intended to be included within the scope of this disclosure as defined in the claims.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and:

FIG. 1 is a schematic illustration of a well component deployment system working in cooperation with an anomaly recognition and tracking system, according to an embodiment of the disclosure;

FIG. 2 is a schematic illustration of an example of a processing system that may be used in cooperation with an anomaly sensor, according to an embodiment of the disclosure;

FIG. 3 is a schematic illustration of an example of an anomaly storage medium, according to an embodiment of the disclosure;

DETAILED DESCRIPTION

Figure 4:
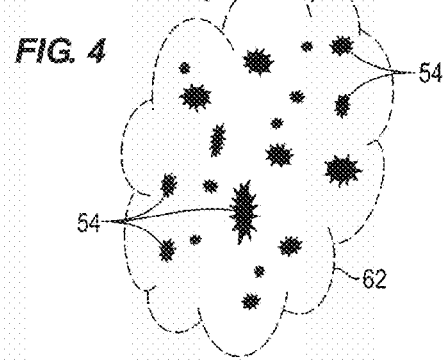
FIG. 4 is a schematic illustration of an example of a natural anomaly library, according to an embodiment of the disclosure.

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible. Through the present disclosure, the terms "anomaly", "anomalies", "defect", or "defects" may be used interchangeably to refer to material irregularity or imperfection, mechanical or corrosion damage of an oilfield pipe or well component, or spurious signal(s) due to faulty electronic sensing. Through the present disclosure, the terms "pipe", "well pipe", "coiled tubing", "well tubular/s", "well component" may be used interchangeably to refer to tubular structure for oilfield applications.

The present disclosure generally relates to a methodology and system for recognition and tracking of anomalies in well components, e.g. well tubulars, and other types of components. The technique comprises sensing for anomalies in the component, and storing detected anomalies in a storage medium. The detected anomalies are matched with stored digital descriptions of anomalies. The stored digital descriptions may comprise anomalies of similar types and/or anomalies previously detected on the specific component being tested. For example, the stored digital descriptions may comprise a library collection of typical anomalies collected during lab testing, yard testing, field inspections, and/or other collection techniques. The stored digital descriptions also may comprise anomalies recorded during a specific inspection job or jobs related to a specific component. This allows the anomalies for that specific component to be tracked during sequential uses. The detected anomalies are ranked according to similarities with respect to the stored digital descriptions regarding general types of anomalies and/or anomalies specific to the component.

The system and methodology described herein focus on an anomaly recognition and tracking program and the efficient construction and implementation of such a program. Additionally, the methodology enables anomaly tracking (both forward and backward) for continuous component, e.g. pipe, monitoring and evaluation. The present methodology also may be used for other types of anomaly recognition, including detection and recognition of spurious signals and detection and recognition of objects, e.g. steel balls, passing through a tubular. In tracking applications, anomalies above a given threshold can be reliably tracked (including the initial occurrence of an anomaly) to monitor the progression and evolution of that anomaly from job to job. This latter capability provides another measure of component, e.g. pipe, fatigue and reliability.

In some embodiments, the system may be used with well tubulars, such as well pipe, jointed pipe, or coiled tubing. An effective way to reduce tubing failures is through real-time inspection and monitoring. The present system and methodology provides a computer-aided operator-independent program for anomaly recognition and tracking via ranking of matching coefficients between detected anomalies and stored anomalies, e.g. digitally stored anomalies. The technique is very useful for coiled tubing, however it has broader applications for facilitating inspection of other oilfield equipment, including high pressure pumping pipes, offshore risers, drill pipes, drill collars, other drilling related tubulars, wireline cables, slickline cables, control lines, seismic cables, and other well and non-well related components. Additionally, various sensor technologies may be employed for detecting anomalies, e.g. defects, in the component being inspected.

In a variety of applications, the sensor technology may comprise magnetic flux leakage sensor technology employing a magnetic flux leakage sensor or sensors. However, a wide variety of other sensors and sensor technologies may be employed separately or in combination with magnetic flux leakage sensors. With respect to applications using magnetic flux leakage sensors, magnetic flux leakage is a volumetric, non-destructive evaluation technique that allows for a quick screening of the component for outer diameter and inner diameter anomalies, e.g. defects. The magnetic flux leakage sensor may be operated while the component, e.g. well tubular, is moving relative to the sensor. For example, magnetic flux leakage sensors may be employed to sense anomalies in well tubulars as they pass through the sensor device during regular operational speeds, e.g. deployment speeds conveying the well tubulars downhole.

Magnetic flux leakage technology is sensitive to metal damage, such as pipe damage, e.g. gouges, dents, pinholes, and other damage. Additionally, magnetic flux leakage sensors are sensitive to other pipe discontinuities, including bias welds, butt welds, and other tubular features. The magnetic flux leakage sensors also may be employed to detect other types of anomalies, such as metal objects passing through the tubing. The anomalies are stored digitally as high density magnetic flux leakage data which can be plotted in three-dimensional space to indicate signatures or patterns indicative of specific anomalies.

Referring generally to FIG. 1, an embodiment of a well system 20 is illustrated although many other well and non-well related embodiments of system 20 may be used depending on the specific application. In the embodiment illustrated, well system 20 comprises a component deployment system 22, e.g. a surface rig, which may be used to deploy a component 24 downhole into a wellbore 26. In this example, the component deployment system 22 is located at an Earth surface 28, which may be a land surface or a sea surface. The component deployment system 22 may be constructed for deployment of various components, including coiled tubing, high pressure pumping pipes, offshore risers, drill pipes, drill collars, other drilling related tubulars, wireline cables, slickline cables, control lines, seismic cables, and other well and non-well related components 24. In the specific example illustrated, deployment system 22 is used to deploy a well tubular 24, such as coiled tubing, drill pipe, or production pipe. The well tubular 24 may be coupled to a variety of other tools 30.

As illustrated, well system 20 also comprises a sensor system 32 having one or more sensors 34, e.g magnetic flux leakage sensors, digital cameras, x-ray sensors, infrared sensors, acoustic sensors, or other suitable sensors. The sensor system 32 is positioned to allow relative movement or motion between the sensor system 32 and the component 24 to facilitate detection of anomalies. Depending on the application, the sensor system 32 may be moved, the component 24 may be moved, or both the sensor system 32 and component 24 may be moved simultaneously to achieve the relative motion. In the example illustrated, the component 24 is a well component which moves past sensor system 32 as the well component 24, e.g. well tubing, is moved downhole into wellbore 26. The sensors 34 of sensor system 32 provide data regarding anomalies to a processor system 36 which processes the data and compares the data to stored digital descriptions of anomalies to determine matches and rankings of those matches.

Depending on the specific application, processing system 36 may have a variety of features and configurations. In the present disclosure, the processing system 36 is employed to build an anomaly library, to run anomaly matching programs, e.g. algorithms, and to recognize and/or track anomalies by ranking matching coefficients. In some applications, the processing system 36 may be located at surface location 28, within or in proximity to wellbore 26, partially within or partially away from the wellbore 26 and at surface location 28, and/or at other suitable locations.

Referring generally to FIG. 2, an example of processing system 36 is illustrated. In this example, processing system 36 is in the form of a computer-based system having a processor 38, such as a central processing unit (CPU). The processor 38 is coupled with sensor or sensors 34 of sensor system 32 via a wired or wireless communication line 40 and is operatively employed to intake sensor data from sensors 34 regarding anomalies detected in component/well tubular 24. Processing system 36 is then able to process that data as desired, e.g. according to a suitable program, algorithm, model, or other appropriate software. For example, the processor 38 may be used to compare data obtained by sensors 34 with stored digital descriptions of anomalies of general types and/or of anomalies previously recorded with respect to the specific component/well tubular 24 being tested.

The processor 38 also may be operatively coupled with a memory 40, e.g. a digital storage medium, employed to store a library or libraries 42 of digital descriptions of anomalies. The processor 38 also may be operatively coupled with an input device 44 and an output device 46. In some applications, processor 38 is used to run software 48, such as software embodying an anomaly matching algorithm 50, which compares data obtained from sensors 34 with stored digital descriptions of types of anomalies (such as those stored in library or libraries 42) and/or of anomalies previously detected on the specific component 24 being tested. Examples of anomaly matching algorithms 50 comprise pattern or picture matching algorithms (which may be analogous to facial recognition algorithms) for comparing the digital pixels associated with a picture of a detected anomaly with the digital pixels of stored digital descriptions/pictures of an anomaly or anomalies. The algorithm 50 also may comprise a magnetic flux leakage algorithm for comparing magnetic flux leakage data profiles of a detected anomaly with stored magnetic flux leakage data profiles. The algorithm 50 may also utilize auxiliary data or information, such wall thickness, depth, etc., to recognizing/tracking anomalies. However, software 48 may comprise a variety of types of models, algorithms, programs, and/or other suitable software depending on the types of sensors 34 employed, types of digital descriptions evaluated, and/or operational parameters for a given application.

By way of example, input device 44 may comprise a variety of devices, such as a keyboard, mouse, voice recognition unit, touchscreen, other input devices, or combinations of such devices. Output device 46 may comprise a visual and/or audio output device, such as a computer display, monitor, or other display medium having a graphical user interface. Additionally, the processing may be performed on a single device or multiple devices on location, away from the sensing location, or with some devices disposed on location and other devices located remotely. The software 48 (in the form of a suitable algorithm 50, model, or other programming) may be used to evaluate data from sensors 34 in real time to provide real-time anomaly detection, tracking, matching, and ranking.

In some applications, processing system 36 and output device 46 may be used to indicate movement of objects through a tubular component 24 and past specific sensors 34. Data indicating these types of anomalies may be presented to an operator through output device 46 via a graphical user interface 52. The raw and/or processed data displayed via graphical user interface 52 may vary substantially depending on the parameters of a given application. For example, sensors 34 and processing system 36 may be designed to output data on parameters, such as anomalies detected, matches with stored digital descriptions of anomalies, and ranking matching coefficients. However, the graphical user interface 52 may have a variety of forms and configurations for displaying many types of data from individual or multiple sensors 34.

Referring generally to FIG. 3, an example of one type of library 42 is illustrated. An embodiment of the present disclosure involves building up an anomaly library, e.g. library 42. The anomaly library 42 comprises a collection of digital descriptions 54 of a variety of anomalies, such as those anomalies that may occur in well tubulars, e.g. well pipe or coiled tubing. In some applications, the digital descriptions 54 may comprise defect descriptions, such as defect signatures 56 (e.g. magnetic flux leakage data signatures) and defect images or pictures 58 (e.g. digitally stored pictures). The defect signatures 56 may be obtained utilizing a plurality of sensor readings or by processing a plurality of sensor readings. The defect images or pictures 58 may be obtained utilizing a hand-held camera, an automatic camera system, or by a special imaging system such as, but not limited to, an infrared camera, an X-ray system or a laser scan system. The defect image or picture 58 may also be represented by sketches or drawings with specified dimensions. The digital descriptions 54 may comprise pictures of anomalies showing their physical size and appearance along with corresponding, non-destructive measurement data. Examples of corresponding, non-destructive measurement data include magnetic flux leakage data profiles and three-dimensional visualization of such measurement data. The library 42 may also comprise auxiliary data such as, but not limited to, wall thickness profile(s).

Library 42 may comprise a plurality of libraries or library segments. For example, library 42 may comprise an anomaly recognition library 60 for anomaly recognition and this type of library may involve substantial anomaly collection and library construction efforts. The anomaly recognition library 60 comprises collected data containing information regarding anomalies, e.g. typical anomalies, collected during numerous previous lab tests, yard tests, field inspections, and other procedures using non-destructive sensor systems, such as magnetic flux leakage sensor-based systems.

Such a library may begin with a limited number of anomaly entries in the form of digital descriptions of those anomalies. Over time, the library can be substantially expanded with continual accumulation of digital descriptions of anomalies accumulated at least in part by data gathered from the sensor(s) 34 and processed by processing system 36. In some applications, the numerous anomalies in the library may be grouped into categories, e.g. gouges, dents, bias welds, pinholes, spurious signals, extra metal, and/or other categories. Under each category, numerous anomaly examples may be included to provide further details about each specific type of collected anomaly. Those details may be related to parameters such as anomaly shape, length, width, depth, orientation, and/or other parameters. As the library is expanded, additions, deletions, and reorganizations of the library may be performed periodically or on an ongoing basis.

Generally, the more comprehensive and accurate the library 42, the more convenient and accurate will be the performance of anomaly recognition during operation of the system 20. There is shown in FIG. 3 a schematic drawing of a library 60 having a variety of stored digital descriptions 54. The illustrated library 42, 60 comprises n anomaly entries and each entry is numbered sequentially for tracking purposes. Additionally, each entry has a graphically presented inspection data-based signature 56, a corresponding camera-taken anomaly image picture 58, and other corresponding notes 54, e.g. inspection date, inspection location, device serial number, pipe string number, pipe diameter, pipe grade, pipe wall thickness, type of operation, fatigue life, and/or other parameters. In this example, an inspection data set is associated with each entry and stored in the digital storage medium 40 for use by software 48 when, for example, anomaly matching algorithm 50 is running.

The library 42 also may comprise an additional library or library segment 62 constructed to facilitate anomaly tracking with respect to specific components 24, e.g. specific well tubulars. A schematic representation of the anomaly tracking library 62 is shown in FIG. 4. This portion of library 42 comprises the anomalies recorded during a specific inspection operation or job. For tracking purposes, an operator may be interested in identifying the origin and/or evolution of specific anomalies among a series of inspection job runs on the same component 24, e.g. on the same pipe string. For this type of anomaly tracking, the operator begins with a selected anomaly of concern recorded during a latest job run and then navigates or reviews data from related inspection job runs, often in a chronological order.

The anomaly tracking involves finding a counterpart of a selected anomaly from the current job run with an anomaly in another job run. The saved digital descriptions of anomalies of a given job run being searched serve as a natural library 62, and FIG. 4 provides a schematic illustration of natural library 62 with a variety of recorded digital descriptions 54 corresponding with specific anomalies. In FIG. 4, the digital description entries are illustrated as distributed randomly but they may be numbered sequentially relative to their positions in the well component so that they can be readily traced individually. Each entry may also be associated with other physical and/or auxiliary parameters such as, but not limited to, wall thickness and depth. The auxiliary parameters may also be used in accurate tracking.

Figure 5:
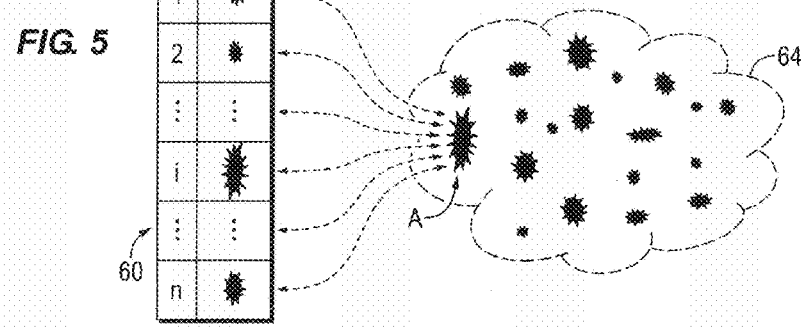
FIG. 5 is a schematic illustration of an example of a matching process performed by a matching algorithm to compare anomalies of a well component collected from a source job with anomalies stored in a digital storage medium, according to an embodiment of the disclosure.

Another portion of the present embodiment may comprise running software 48 to determine matching coefficients. According to a specific example, an anomaly matching algorithm 50 may be run on processor system 36, as represented by FIG. 5. In an operational example, the anomaly matching algorithm 50 is run with respect to a specific anomaly, A, recorded during an inspection job (the so-called source job) and compared with each individual entry in the anomaly library 42. Depending on the objective of the anomaly matching, various scenarios may emerge. In an anomaly recognition scenario, for example, a similarity of the anomaly (such as the type and configuration of the selected anomaly A) is determined. For this task, the anomaly library 60 (see FIG. 3) is employed and the anomaly matching algorithm 50 runs between the present job (source job) 64 and the anomaly library 60 as represented schematically in FIG. 5. The anomaly matching algorithm 50 may be performed in real-time, such as during field inspection or yard inspection, or post-job (after an inspection job is done). The results of anomaly matching algorithm 50 may be used by the operator of the system 20 as a basis for a variety of operational decisions such as, but not limited to, temporarily stopping the operations to perform prove-up of the detected anomaly or anomalies, altering the operational schedule to increase safety margin, repairing the defect, or retiring the well tubular 24 from service. The anomaly matching algorithm 50 may also be utilized to filter those signals that may not be triggered by an anomaly but by faulty electronics or the like, which filtered signals may also be part of the anomaly library 60. In an embodiment, the anomaly matching algorithm 50 may be utilized for real-time defect identification by first saving the anomaly defect signatures 56 from the acquisition software 48. The saved anomaly defect signatures 56 may then processed and/or read by a dedicated interpretation software, such as the software 48 embodying the anomaly matching algorithm 50, to perform defect identification. Such real-time acquisition and identification may be performed on the same processing system 36, on different processing systems 36 in the same network or remotely, such as via a networked processing system 36 or the like. In an embodiment, the anomaly matching algorithm 50 may be utilized for real-time defect identification by performing data acquisition and defect identification using the same software, such as the software 48 embodying the anomaly matching algorithm 50.

Figure 6:
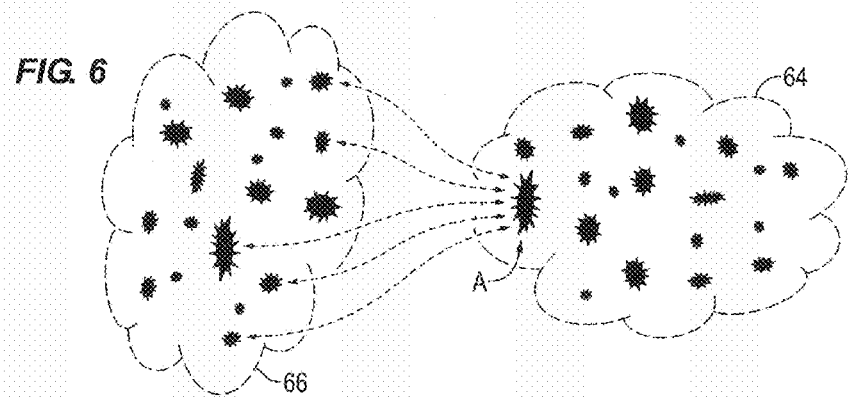
FIG. 6 is a schematic illustration of an example of a matching process performed by a matching algorithm to compare anomalies of a well component collected from a source job with anomalies collected during a target job, according to an embodiment of the disclosure.

For anomaly tracking, however, counterparts of the selected anomaly A are identified in a target job 66 that is either before or after the source job 64 in which anomaly A was recorded, with both job 64 and job 66 performed on the same well component at two different times. In this case, the anomaly library 62 of target job 66 (see FIG. 4) is employed, and the anomaly matching algorithm 50 runs between the source and target jobs as shown schematically in FIG. 6. In this manner, a selected anomaly A from a specific job utilizing component 24, e.g. well tubulars 24, may be compared to that same anomaly on the same component 24 in a different job performed either earlier or later. This capability enables tracking of specific anomalies for a given component 24 over multiple and/or during sequential jobs. Anomaly tracking may be performed in real-time such as during field inspection or yard inspection, or post-job (after an inspection job is done). Anomaly tracking provides the ability to continuously monitor the same defect within one job or from job to job, providing qualitative and quantitative evidence for operational decisions, such as pipe management decisions such as, but not limited, to temporarily stopping the operations to perform prove-up, altering the operation schedule for safety, repairing the defect, or retiring the pipe from service. Anomaly tracking may be accomplished by first saving the anomaly defect signatures 56 from the acquisition software 48. The saved anomaly defect signatures 56 may then processed and/or read by a dedicated interpretation software, such as the software 48 embodying the anomaly matching algorithm 50, to perform defect tracking. Such real-time acquisition and tracking may be performed on the same processing system 36, on different processing systems 36 in the same network or remotely, such as via a networked processing system 36 or the like. In an embodiment, real-time defect tracking may be performed by performing data acquisition and defect tracking using the same software, such as the software 48. In an embodiment, data acquisition, anomaly identification, and anomaly tracking may each be performed using the same software 48.

Figure 7:
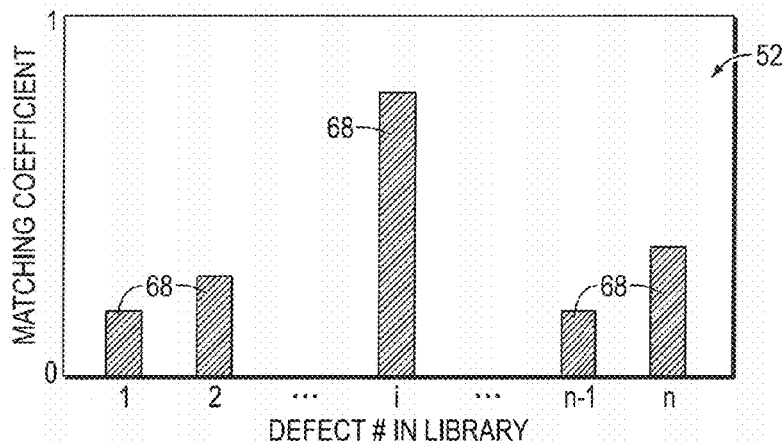
FIG. 7 is an illustration of an example diagram showing matching coefficient rankings between anomalies detected and anomalies stored in a digital storage medium, according to an embodiment of the disclosure.

Another portion of the present disclosure may comprise recognizing and/or tracking anomalies by ranking matching coefficients, as represented graphically in FIG. 7. A matching coefficient refers to the level of similarity between two signal patterns, which may be calculated as co-relation coefficient between these two signals. FIG. 7 also provides an example of a graphical user interface 52 that may be displayed via output device 46. According to an embodiment, the ranking may comprise ranking matching coefficients to determine highly ranked matches between detected anomalies, e.g. anomaly A detected in the component 24 by the anomaly sensors 34, and the digital descriptions 54 of anomalies stored in library 42 of digital storage medium 40.

In this example, if we let Bj, j=1, 2, . . . i, n−1, n where n represents entries in the anomaly library 42, as the jth anomaly in the library, then n matching coefficients, ABj, are obtained between the selected anomaly A and the collection of library entries Bj. The matching coefficients ABj are then ranked, as illustrated schematically in FIG. 7 via graph bars 68. The ranking from highest to lowest with respect to the matching coefficient enables identification of relatively highly matched anomalies in the library 42 (e.g. either or both library 60 and library 62) with the selected anomaly A. For anomaly recognition, the highest-ranking matches represent the probable anomaly type and configuration with respect to the selected anomaly A. For anomaly tracking, the high-ranking match may represent a high likelihood of being the counterpart of the selected anomaly A within a target job, thus enabling a higher level of accuracy in matching and tracking specific anomalies for a specific component 24 as the component 24 is used over multiple jobs. For anomaly tracking of the counterpart in a target job of a selected anomaly in a source job for the same well component, besides the matching coefficients, additional information such as wall thickness, depth, etc., may be used together to determine the matched or matching anomaly.

Figure 8:
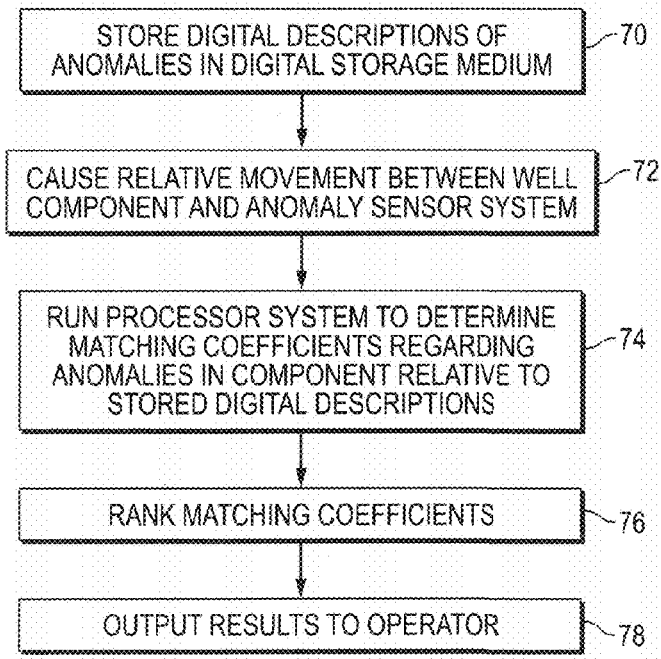
FIG. 8 is a flowchart representing an operational example of anomaly recognition and tracking, according to an embodiment of the disclosure.

Referring generally to FIG. 8, an operational example of the technique is illustrated in flowchart form. In this non-limiting example, digital descriptions 54 of anomalies are stored in digital storage medium 40, as represented by block 70. A well component, e.g. a well tubular 24, and a sensor or sensors 34 are then moved relative to each other to enable detection of anomalies in the well component, as represented by block 72. The processor system 36 is then run to process the data obtained from sensors 34. For example, an anomaly matching algorithm 50 may be run to determine matching coefficients between anomalies in the well component 24 and stored digital descriptions 54, as represented by block 74.

The matching coefficients are then ranked to determine the highest probabilities of a match between a given anomaly A in the well component 24 and anomalies represented by digital descriptions 54, as represented by block 76. The digital descriptions 54 may be related to digital descriptions stored for anomaly recognition and/or for anomaly tracking. The ranking results are output to an operator via, for example, graphical user interface 52, as represented by block 78.

As described herein, the overall system 20, including sensor system 32 and processing system 36, may be used in testing a wide variety of tubulars and other components, including coiled tubing and other types of well tubing. Depending on the specifics of a given application, a variety of sensor systems 32, processing systems 36, software 48, and/or other components may be utilized to facilitate anomaly recognition and tracking via matching coefficient ranking.

Additionally, the software 48 may incorporate a variety of algorithms 50 able to perform digital comparisons of detected anomalies and stored digital descriptions representing anomalies. The algorithm driven digital comparison may utilize comparisons of pixels from digital pictures taken by sensors/cameras, magnetic flux leakage data profiles obtained via magnetic flux leakage sensors, other digitized data, and/or combinations of data types. Additionally, the digital data obtained via sensor system 32 during testing of a given component 24 may be obtained at various stages of a well or non-well operation. The digital data related to anomalies on the tested component 24 may be compared with digital descriptions stored in digital storage medium 40 in real time and/or periodically.

Embodiments of a system and/or method disclosed herein comprise a probable defect type and/or matching counterpart, which then may be presented based on the similarity ranking with the aid of auxiliary secondary data, such as, but not limited to, wall thickness, depth, etc. The entire methodology may be automated and/or computerized and made extremely automatic and efficient. Embodiments of the present disclosure have the benefit of minimizing personnel exposure to hazardous environment, as well as reducing operation interruption for anomaly prove-up, which may ultimately improve service quality. The results of such a system and/or method of the present disclosure may then be used to make certain operation and pipe management decisions, such as time for pipe replacement and the like.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A method for anomaly recognition and tracking, comprising:
   storing digital descriptions of anomalies in a digital storage medium;
   providing a well component;
   positioning an anomaly sensor adjacent the well component;
   moving the well component and the anomaly sensor relative to each other to detect anomalies in the well component;
   running an anomaly matching algorithm on a processor system to determine at least one matching coefficient between the anomalies in the well component and a digital description of the anomalies stored in the digital storage medium; and
   ranking the matching coefficients to determine highly ranked matches between anomalies detected in the well component via the anomaly sensor and the digital descriptions of anomalies stored in the digital storage medium.

2. The method as recited in claim 1, wherein storing comprises accumulating digital descriptions of anomalies during inspections of well components.

3. The method as recited in claim 1, wherein storing comprises storing digital descriptions according to specific well components to enable monitoring of each specific well component used repetitively for multiple jobs.

4. The method as recited in claim 1, wherein storing comprises storing digital pictures of anomalies.

5. The method as recited in claim 1, wherein storing comprises storing magnetic flux leakage data profiles of anomalies.

6. The method as recited in claim 1, wherein moving the well component comprises moving a well pipe past the anomaly sensor.

7. The method as recited in claim 1, wherein moving the well component comprises moving a well pipe past the anomaly sensor as the well pipe is conveyed downhole into a wellbore.

8. The method as recited in claim 1, wherein storing comprises storing at least an anomaly dimension or an anomaly orientation.

9. The method as recited in claim 1, wherein running comprises determining matching coefficients regarding a similarity of the anomalies.

10. The method as recited in claim 1, wherein ranking comprises outputting graphically both anomaly matches and match ranking.

11. A method for anomaly recognition and tracking, comprising:
    providing a well tubular;
    positioning an anomaly sensor adjacent the well tubular;
    deploying the well tubular downhole into a wellbore
    sensing for anomalies with the anomaly sensor as the well tubular is deployed downhole into the wellbore;
    storing detected anomalies in a digital storage medium;
    matching detected anomalies with stored digital descriptions of anomalies and with anomalies detected on the well tubular during a job run; and
    ranking the detected anomalies according to similarities with respect to the stored digital descriptions of anomalies.

12. The method as recited in claim 11, wherein positioning comprises positioning a magnetic flux leakage sensor adjacent the well tubular and wherein sensing comprises sensing using the magnetic flux leakage sensor to detect anomalies.

13. The method as recited in claim 11, wherein storing comprises storing detected anomalies as additional stored digital descriptions to expand an anomaly library of stored digital descriptions.

14. The method as recited in claim 13, wherein running comprises running a pattern matching algorithm to match signal patterns of anomalies detected from a job with signal patterns of anomalies already stored in the digital storage medium.

15. The method as recited in claim 11, wherein ranking comprises outputting data to a user regarding matching and relative rankings of those matches.

16. The method as recited in claim 11, further comprising tracking an anomaly progression for the well tubular as the well tubular is used over a series of jobs.

17. The method as recited in claim 11, wherein sensing comprises sensing for anomalies in coiled tubing as the coiled tubing is deployed downhole.

18. The method as recited in claim 11, wherein running further comprises tracking the progress of anomalies for a well component as the well component is used over a series of job.

19. A system for detecting anomalies, comprising:
- a tubular deployment system to deploy a tubular downhole into a wellbore;
- a sensor positioned along the tubular to monitor for anomalies related to the tubular;
- a storage medium which stores digital descriptions of characteristics of anomalies; and
- a processor to compare data from the sensor with the digital descriptions stored in the storage medium, the processor configured to output a ranking of comparisons to indicate a strength of a match between data from the sensor and the digital descriptions.

20. The system as recited in claim 19, wherein the sensor is used to detect anomalies as the tubular is moving into or retrieved from a well bore.

\* \* \* \* \*